United States Patent
Monty et al.

(10) Patent No.: US 10,045,833 B2
(45) Date of Patent: *Aug. 14, 2018

(54) APPARATUS AND METHOD FOR CONTROLLED FLUID COOLING DURING LASER BASED DENTAL TREATMENTS

(71) Applicant: Convergent Dental, Inc., Natick, MA (US)

(72) Inventors: Nathan P. Monty, Charlton, MA (US); Charles H. Dresser, Newton, MA (US)

(73) Assignee: Convergent Dental, Inc., Needham, MA (US)

( * ) Notice: Subject to any disclaimer, the term of this patent is extended or adjusted under 35 U.S.C. 154(b) by 286 days.

This patent is subject to a terminal disclaimer.

(21) Appl. No.: 13/894,067

(22) Filed: May 14, 2013

(65) Prior Publication Data

US 2013/0323672 A1  Dec. 5, 2013

Related U.S. Application Data

(60) Provisional application No. 61/646,579, filed on May 14, 2012.

(51) Int. Cl.
*A61C 1/00* (2006.01)
*A61C 19/06* (2006.01)
(Continued)

(52) U.S. Cl.
CPC .......... *A61C 1/0069* (2013.01); *A61C 1/0046* (2013.01); *A61C 1/0061* (2013.01);
(Continued)

(58) Field of Classification Search
CPC ... A61C 1/0069; A61C 1/0046; A61C 1/0061; A61C 19/063; A61C 1/052; A61C 1/087; A61C 1/0007; A61C 1/0084; A61B 18/20
(Continued)

(56) References Cited

U.S. PATENT DOCUMENTS 4,276,023 A * 6/1981 Phillips ............... A61C 1/0061
433/100
4,711,630 A 12/1987 Durr et al.
(Continued)

FOREIGN PATENT DOCUMENTS

DE        19533350 A1    5/1996
DE     102008053964 A1    5/2010
(Continued)

OTHER PUBLICATIONS

International Search Report and Written Opinion for International Patent Application No. PCT/US2013/040945 dated Jan. 14, 2014 (18 pages).
Assa, Shlomo, et al. "Ablation of Dental Hard Tissues with a Microsecond Pulsed Carbon Dioxide Laser Operating at 9.3-(mu)m with an Integrated Scanner," Lasers in Dentistry XIV, Proc. of SPIE, vol. 6843, 2008, pp. 1-7.
(Continued)

*Primary Examiner* — Nathan J Jenness
(74) *Attorney, Agent, or Firm* — Goodwin Procter LLP

(57) ABSTRACT

A system for dental tissue treatment includes a system for directing a laser beam to an area of dental tissue to be treated, and a fluid-delivery system for directing and controlling a flow of a fluid. The fluid is directed to at least a portion of the area to be treated and the fluid flow is controlled to substantially prevent both a change in laser energy absorption by the dental tissue and attenuation of treatment efficiency due to fluid interference with the laser beam. The fluid present in at least a portion of the area to be treated may prevent or reduce the likelihood of melting of enamel in that area.

28 Claims, 8 Drawing Sheets

(51) Int. Cl.
    *A61C 1/05*           (2006.01)
    *A61C 1/08*           (2006.01)
    *A61C 17/02*         (2006.01)

(52) U.S. Cl.
    CPC ............ *A61C 19/063* (2013.01); *A61C 1/052* (2013.01); *A61C 1/087* (2013.01); *A61C 17/0217* (2013.01)

(58) Field of Classification Search
    USPC .......................................................... 606/2
    See application file for complete search history.

(56) References Cited

U.S. PATENT DOCUMENTS

| | | | |
|---|---|---|---|
| 4,826,431 A | 5/1989 | Fujimura et al. | |
| 4,874,315 A | 10/1989 | Featherstone et al. | |
| 5,051,823 A | 9/1991 | Cooper et al. | |
| 5,310,471 A | 5/1994 | Markle et al. | |
| 5,342,198 A | 8/1994 | Vassiliadis et al. | |
| 5,364,390 A | 11/1994 | Taboada et al. | |
| 5,401,171 A | 3/1995 | Paghdiwala | |
| 5,454,807 A * | 10/1995 | Lennox ................. | A61B 18/24 606/14 |
| 5,456,603 A | 10/1995 | Kowalyk et al. | |
| 5,538,425 A | 7/1996 | Reeves et al. | |
| 5,622,501 A | 4/1997 | Levy | |
| 5,748,663 A | 5/1998 | Chenausky | |
| 5,833,456 A | 11/1998 | Davis et al. | |
| 5,846,080 A | 12/1998 | Schneider | |
| 5,897,314 A | 4/1999 | Hack et al. | |
| 6,083,218 A | 7/2000 | Chou | |
| 6,198,762 B1 | 3/2001 | Krasnov | |
| 6,270,342 B1 | 8/2001 | Neuberger et al. | |
| 6,339,913 B1 | 1/2002 | Leon Fong et al. | |
| 6,343,174 B1 | 1/2002 | Neuberger | |
| 6,482,199 B1 | 11/2002 | Neev | |
| 6,558,372 B1 | 5/2003 | Altshuler | |
| 6,558,374 B1 | 5/2003 | Brugger et al. | |
| 6,607,524 B1 | 8/2003 | LaBudde et al. | |
| 6,610,053 B1 | 8/2003 | Rizoiu et al. | |
| 6,663,386 B1 | 12/2003 | Moelsgaard | |
| 6,679,837 B2 | 1/2004 | Daikuzono | |
| 6,709,269 B1 | 3/2004 | Altshuler | |
| 6,758,844 B2 | 7/2004 | Neuberger | |
| 7,163,400 B2 | 1/2007 | Cozean et al. | |
| 7,270,543 B2 | 9/2007 | Stookey et al. | |
| 7,632,264 B2 | 12/2009 | Schafer | |
| 7,748,979 B2 | 7/2010 | Nahlieli | |
| 7,813,790 B2 | 10/2010 | de Josselin de Jong et al. | |
| 8,029,501 B2 | 10/2011 | Miller | |
| 9,011,416 B2 * | 4/2015 | Monty ................. | A61C 1/0069 606/2 |
| 9,011,417 B2 * | 4/2015 | Monty ................. | A61C 1/0069 606/2 |
| 2003/0100824 A1 | 5/2003 | Warren et al. | |
| 2004/0024388 A1 | 2/2004 | Altshuler | |
| 2004/0209222 A1 * | 10/2004 | Snyder ................. | A61C 17/02 433/80 |
| 2004/0259053 A1 | 12/2004 | Bekov et al. | |
| 2005/0256517 A1 * | 11/2005 | Boutoussov ....... | A61B 17/3203 606/16 |
| 2006/0142745 A1 | 6/2006 | Boutoussov | |
| 2006/0189965 A1 | 8/2006 | Litvak et al. | |
| 2006/0195072 A1 | 8/2006 | Miller | |
| 2007/0121786 A1 | 5/2007 | Okawa et al. | |
| 2007/0189353 A1 | 8/2007 | Monty | |
| 2007/0265605 A1 | 11/2007 | Vaynberg et al. | |
| 2008/0021441 A1 | 1/2008 | Altshuler et al. | |
| 2008/0138764 A1 | 6/2008 | Rizoiu | |
| 2008/0160477 A1 | 7/2008 | Stookey et al. | |
| 2009/0061391 A1 | 3/2009 | Lukac et al. | |
| 2009/0227991 A1 | 9/2009 | Dick et al. | |
| 2009/0322541 A1 | 12/2009 | Jones et al. | |
| 2010/0021867 A1 | 1/2010 | Altshuler et al. | |
| 2010/0036535 A1 * | 2/2010 | Feine ................. | A61C 1/0061 700/282 |
| 2010/0106146 A1 | 4/2010 | Boitor et al. | |
| 2010/0137851 A1 * | 6/2010 | Lin ....................... | A61B 18/20 606/10 |
| 2010/0185188 A1 | 7/2010 | Boutoussov et al. | |
| 2010/0190129 A1 | 7/2010 | Paz | |
| 2010/0227296 A1 | 9/2010 | Mandelis et al. | |
| 2010/0228222 A1 | 9/2010 | Williams et al. | |
| 2011/0059417 A9 * | 3/2011 | Rizoiu ................. | A61C 1/0046 433/80 |

FOREIGN PATENT DOCUMENTS

| | | |
|---|---|---|
| DE | 102009005194 A1 | 7/2010 |
| EP | 0437955 A1 | 7/1991 |
| EP | 2281528 A1 | 2/2011 |
| FR | 2773619 A1 | 7/1999 |
| JP | H07155335 A | 6/1995 |
| JP | H10277057 A | 10/1998 |
| JP | 2001161713 A | 6/2001 |
| JP | 2001-309927 A | 11/2001 |
| JP | 3638191 B2 | 4/2005 |
| JP | 05245165 B2 | 7/2013 |
| KR | 100767768 B1 | 10/2007 |
| WO | WO-97/10768 A2 | 3/1997 |
| WO | WO-2004/006793 A1 | 1/2004 |
| WO | WO-2007/038975 A1 | 4/2007 |
| WO | WO-2008072033 A1 | 6/2008 |
| WO | WO-2009/052866 A1 | 4/2009 |
| WO | WO-2010/083825 A1 | 7/2010 |
| WO | WO-2011/014802 A2 | 2/2011 |

OTHER PUBLICATIONS

Fan, Kenneth, et al. "A High Repetition Rate TEA CO2 Laser Operating at lambda=9.3-(mu)m for the Rapid and Conservative Ablation and Modification of Dental Hard Tissues," Lasers in Dentistry XII, Proc. of SPIE, vol. 6137, 2006, pp. 1-9.

International Search Report and Written Opinion for International Patent Application No. PCT/US2010/043968 dated Apr. 20, 2011 (8 pages).

International Search Report and Written Opinion for International Patent Application No. PCT/US2011/023483 dated Jan. 25, 2012 (15 pages).

International Search Report and Written Opinion for International Patent Application No. PCT/US2012/053684 dated Mar. 4, 2013 (14 pages).

Visuri et al., "Erbium Laser Ablation of Dental Hard Tissue: Effect of Water Cooling," Abstract downloaded on May 4, 2016, 1 page.

Extended European Search Report on Patent Application No. 13790541.0 dated Feb. 3, 2016, 7 pages.

Sensiron, The Sensor Company, "Liquid Flow Switch and Bubble Detector" LG01-2000Axxx Datasheet, 4 pages (Feb. 2015).

Official Action for Japanese Patent Application No. 2015-512754, dated May 21, 2018.

* cited by examiner

PARAMETERS CHART

| FEATURE | MIN VAL. | NOMINAL VAL. | MAX VAL. | UNIT |
|---|---|---|---|---|
| WAVELENGTH | 5 | 9.25 - 9.6 | 15 | µm |
| PULSE ENERGY | 0.1 | 11 | 30 | mJ |
| PULSE LENGTH | 0.1 | 20 | 50 | µsec |
| PULSE REPETITION RATE | 0.1 | 10 | 20 | kHz |
| FLUENCE AT FOCUS | 0.14 | 7.94 | 50 | J/cm$^2$ |
| ENERGY PROFILE | | TOP HAT, GAUSSIAN, DONUT, RANDOM | | |
| CONDITION OF TOOTH | | CLEAN CUT, STERILIZED, FRACTURED | | |
| PRESSURE OF THE COOLANT | 0 | 20 | 80 | psi |
| GAS | 0 | 20 | 80 | psi |
| LIQUID | 0 | 20 | 40 | psi |
| VOLUMETRIC FLOW RATE OF THE COOLANT | 0 | 1 | 10 | mm$^3$/min |
| GAS | 0 | 1 | 10 | mm$^3$/min |
| LIQUID | 0 | 5 | 20 | ml/min |
| PERCENTAGE OF LIQUID IN FLUID | > 0 | 50 | < 100 | |
| TYPE OF FLOW | | CONTINUOUS, BURSTS, ALTERNATING | | |
| FREQUENCY OF BURSTS | 0 | 1 | 10 | Hz |
| DURATION OF A BURST | 0 | 100 | 1000 | ms |
| FLUID TYPE | | AIR & WATER MIX, WATER MAY HAVE SALT | | |
| EXAMPLES OF ADDITIVES | | PEROXIDE, MEDICATIONS, PIGMENTS, MINERALS | | |
| NUMBER OF NOZZLES IN AN ARRAY | 1 | 4 | 10 | |
| SHAPE OF AN ARRAY OF NOZZLES | | SQUARE, CIRCLE, ELLIPSE | | |
| ANGULAR RANGE WITHIN WHICH A NOZZLE CAN BE ORIENTED | 0 | 45 | 90 | degrees |
| NOZZLE ORIFICE DIAMETER | 0.008 | 0.015 | 0.15 | in |
| SIZE OF IMPINGING AREA CORRESPONDING TO ONE NOZZLE | 0.000050 | 0.0005 | 0.053 | in$^2$ |
| SHAPE OF IMPINGING AREA CORRESPONDING TO ONE NOZZLE | | CIRCLE | | |
| FLOW PATTERN | | DROPLET, COLUMN, MIST | | |
| STAND OFF BETWEEN THE NOZZLES AND THE SURFACE OF THE TOOTH | 2 | 9 | 50 | mm |

FIG. 5

APPARATUS AND METHOD FOR CONTROLLED FLUID COOLING DURING LASER BASED DENTAL TREATMENTS

CROSS REFERENCE TO RELATED APPLICATIONS

This application is related to and claims the benefit of priority to U.S. Provisional Patent Application Ser. No., 61/646,579 filed on May 14, 2012, the entirety of which is hereby incorporated by reference.

FIELD OF THE INVENTION

This invention relates to coolant systems and in particular to coolant systems for laser-based dental treatment.

BACKGROUND

Some dental treatment systems use lasers, e.g., for cutting tooth enamel. It may be beneficial to replace drills conventionally used in dental treatment with laser-based systems, in part because lasers can provide for better control of the process of cutting and removing material from a tissue to be treated, such as a tooth. Also, laser-based systems are typically less noisy and may produce less vibrations than a conventional drill. Lasers have also been found to be useful in the removal of dental material with less amount of local anesthetic than that required when the procedure is performed with a drill. For these reasons many in the dental industry have expected for some time that laser based systems will replace the drill based dental treatment systems.

The Food and Drug Administration (FDA) has approved seven different types of lasers and laser diodes for use in dental applications. Lasers used to treat soft tissue are chosen according to the water absorption characteristics of the laser, and various other characteristics so that the blood is cauterized and bleeding is minimized. Many of the dental treatment systems, however, cut the enamel or hard tissue using lasers that exhibit high water absorption. Typically, the applied laser energy is absorbed in water in tooth enamel (about 4% by volume), causing the water to vaporize, and the resulting steam causing to facture the hard tissue/enamel and thus removing a portion of the enamel from the tooth. Because the laser wavelength is chosen such that a significant portion of the laser energy is strongly absorbed by water, a common problem with such systems is that the cutting operation is slow, due to the low percentage of water in the enamel. In fact, this method of removing dental hard tissue is often considerably slower than using dental drills and many dental procedures are completed in less time by an operator/dentist using a conventional drill than by using a laser that operates by absorption of laser energy in water. For this reason may practitioners choose not to use laser based systems for dental treatment, and as such the benefits that laser based treatment can offer are not widely available at present.

Laser wavelengths in the range of 5 to 15 µm are strongly absorbed by the hydroxyapatite that makes up to about 96% of tooth enamel by weight. Therefore, using lasers in the range of about 5 µm up to about 15 µm can result in faster cutting of hard tissue than that using known laser based dental treatment systems. As explained below, cooling is particularly important in using lasers in the 5 to 15 µm range.

The use of a fluid to assist in cleaning during cutting, e.g., for removing particles created during the cutting operation is known. Such fluids may also be used for cleaning prior to and following the cutting operation. In general in laser-based dentistry, without adequate cooling enamel melts when ablated by a laser of any wavelength, forming non-apatite CaP phases. Therefore, when a laser is used for cutting, a fluid can be used to cool the tissue within the treatment area and/or the surrounding area, to prevent thermal damage thereto, in addition to cleaning.

When the laser is used to fracture the tooth structure by water vaporization, water provided by the system to cool the treatment area can interfere with the laser beam without a significant reduction in material removal rates. This is because the coolant, that may absorb the laser radiation and vaporize can serve to remove hard tissue material by imparting disruptive forces to the treatment area. In some systems, the coolant system is intentionally configured such that the coolant interferes with the laser beam to impart disruptive forces on dental hard tissue. In some laser based dental treatment systems, the coolant is provided only to avoid or minimize the melting of the enamel, without regard to whether the coolant interferes with the ablation operation of the laser beam. Some systems that deliver coolant between laser pulses do not provide forced convective cooling from the surface of the dental region being treated at or nearly at the time the surface is being heated. This can cause the treated surface to experience thermal cycles, heating during laser pulses and cooling in between such pulses.

A dental laser system in which ablation occurs, at least in part, due to absorption of the laser energy in the hydroxyapatite of the hard tissue is likely to experience a marked reduction in material removal rate when a cooling fluid interferes with the laser. In such systems, providing unregulated quantities of water or other coolants is often not a beneficial solution to solve the problem of the melting of the enamel. This is because hydroxyapatite absorbs laser energy at 9.3 to 9.6 µm (which can be classified mid to far infrared range of the laser wavelength) but water also absorbs laser energy at 9.3 to 9.6 µm, and as such, the cooling fluid may significantly attenuate the laser power used for ablation. Therefore, an excess amount of water can interfere with the cutting operation of the laser beam.

In addition, though the melting of the enamel can decrease the efficiency of cutting in general, this problem can be significant when mid to far infrared lasers are used. This is predominantly because the CaP phase structure has a completely different absorption characteristic than hydroxyapatite such that far-infrared 9.3-9.6 µm energy goes from being highly absorbed to virtually not absorbed in the CaP phases. Therefore, this shift in absorption mechanism can make the cooling and ablation of enamel at mid to far-infrared wavelengths far more critical than near-infrared (e.g., conventional) wavelengths where the absorption mechanism is water. Because the ablation of the hydroxyapatite and non-apatite CaP phases is not that dissimilar, some enamel melting that can be tolerated when cutting with near infrared (conventional) laser energy, because the ablation is generally caused by evaporated water. It is highly desirable to avoid such melting when mid to far infrared energy laser is used for ablation because the CaP phases can substantially mitigate or even prevent absorption of the laser energy in the hard tissue to be removed.

As such, there is a need for improved systems and methods to control the fluid used to cool the tissue during laser processing thereof to provide for sufficient removal rates while substantially preventing melting of the enamel.

SUMMARY OF THE INVENTION

In various embodiments, a system and a method in accordance with the present invention facilitates effective dental treatment in which the risk of melting of the enamel by a laser beam is mitigated or eliminated without significantly impacting the efficiency of cutting the dental tissue. This is achieved, in part, by regulating the flow of a coolant fluid such that an amount of fluid present in the treatment area is adequate to minimize the risk of melting of the enamel, but is not so excessive as to interfere with the laser beam by absorbing a significant portion of the laser energy. Specifically, because molten enamel can cover hydroxyapatite, and thus substantially prevent absorption of the laser energy thereby, the system and method ensure that an amount of water/coolant that is sufficient to inhibit or minimize melting of the enamel is present in the treatment area. The amount of water/coolant is minimized, however, so that the portion of radiation absorbed into the water/coolant is minimized and absorption of the laser energy by the hydroxyapatite/enamel to be removed is maximized or maintained near the peak absorption. As a result, the portion of the generated laser energy that is utilized for ablation can be maximized so that the cost and/or duration of the mid to far-infrared laser based treatment is minimized, while preventing melting of the enamel. As part of regulating the flow of the coolant fluid, both the location and amount of cooling fluid may be controlled. Various embodiments may also employ computer controlled laser beam delivery.

Often, as ablation by a laser progresses, a hole or depression forms in the treatment area (surface of the tooth, hard tissue, etc.). Therefore, it is beneficial that the coolant fluid spray is formed such that the coolant fluid wets the surface exposed by ablation, to ensure enamel melting does not occur therein, and non-apatite CaP phases are not formed over the exposed surface. It must also be ensured, however, that coolant fluid pooling is avoided. The coolant fluid pooling may lead to increased absorption of laser energy in the pooled coolant fluid and correspondingly decreased hydroxyapatite ablation rates. Moreover, interaction of water (coolant fluid in general) with the infrared laser beam prior to impingement thereof on the enamel surface can lead to additional absorption of the laser energy in the water, and even less hydroxyapatite absorption. Therefore it is advantageous to ensure that as little coolant spray or mist as possible interacts or intersects with the infrared laser light delivered to the treatment area.

Accordingly, in one aspect, various embodiments feature an apparatus for dental tissue treatment. The apparatus includes a system for directing a laser beam to an area of dental tissue to be treated. The apparatus also includes a fluid-delivery system for directing and controlling a flow of a fluid to at least a portion of the area to be treated to substantially prevent both a change in laser energy absorption by the dental tissue and attenuation of treatment efficiency due to fluid interference with the laser beam. The fluid delivered to at least a portion of the area to be treated may prevent melting of enamel in that area, or may significantly reduce the risk of such melting.

In some embodiments, the fluid includes a liquid and a gas, and the fluid-delivery system may be configured to adjust a proportion of a volume of the liquid with respect to a volume of the fluid. The liquid may include or consist essentially of water. Alternatively, or in addition, the liquid may include one or more of a salt, a peroxide, a medication, a pigment, a mineral, a cutting chemical, and a surfactant. The gas may include or consist essentially of air.

In some embodiments, the fluid-delivery system controls (e.g., using a valve) the flow of the fluid. The fluid-delivery system may be configured to provide a sufficient amount of fluid to substantially prevent the melting of the dental tissue. The fluid-delivery system may also be configured to limit an amount of fluid delivered to the treatment area to limit absorption of the laser beam energy in the fluid.

The fluid may include or consist essentially of a liquid, and the fluid-delivery system may be configured (e.g., using a valve) to adjust a rate of flow of the liquid. In some embodiments, the fluid-delivery system is configured to adjust a pressure of the liquid flow in the range from about 0 psi up to about 40 psi. The fluid-delivery system may also be configured to switch the liquid flow on and off, so as to deliver a liquid burst or a series of bursts. The frequency of switching may be up to about 10 Hz, and a duration of one liquid burst may be up to about 1000 milliseconds.

In some embodiments, the fluid includes or consists essentially of a gas, and the fluid-delivery system (e.g., a valve) is configured to adjust a rate of flow of the gas. Alternatively or in addition, the fluid-delivery system may be configured to adjust a pressure of the gas flow in the range from about 0 psi up to about 80 psi. The fluid-delivery system may be configured to switch the gas flow on and off, so as to deliver a gas burst. A gas burst may be delivered alternately with the delivery of a liquid droplet or burst such that the liquid may provide cooling, and the gas burst removes any excess amount of liquid, that may interfere with the laser beam, from the treatment area/region. The frequency of switching may be up to about 10 Hz, and a duration of one gas burst can be up to about 1000 milliseconds.

In some embodiments, the fluid-delivery system is configured (e.g., using a valve) to adjust a rate of flow of the fluid. For example, the fluid-delivery system may be configured to adjust a pressure of the fluid flow in a range from about 0 psi up to about 80 psi. In some embodiments, two valves may be used—one to control/regulate the flow of a liquid and a second valve to control/regulate the flow of a gas, the liquid and the gas forming the coolant fluid.

In some embodiments, the fluid-delivery system includes a pressure relief regulator for controlling the flow of the fluid, and the fluid includes a gas. The pressure relief regulator may be configured to adjust a pressure of the gas flow in the range from about 0 psi up to about 80 psi. In some embodiments, the pressure relief regulator is configured to adjust a pressure of the gas flow in one or more of a range from about 0 psi up to about 5 psi, causing the fluid to form a droplet at delivery, a range from about 5 psi up to about 15 psi, causing the fluid to form a column at delivery, and a range from about 15 psi up to about 80 psi, causing the fluid to form a mist at delivery.

The fluid-delivery system may include a positive displacement pump for controlling the flow of the fluid, and the fluid may include or consist essentially of a liquid. The positive displacement pump may include a peristaltic pump. The positive displacement pump may operate at a frequency of up to about 750 rpm, and the frequency of the pump can control a rate of flow of the liquid. In some embodiments, the fluid delivery system includes a fluid flow switch that can detect the presence of the fluid flow and/or the presence of bubbles in the fluid flow. The fluid flow switch may be adapted to control the laser beam if a lack of fluid flow is detected and/or a fluid flow including bubbles is detected.

In some embodiments, the fluid-delivery system includes a nozzle forming one or more orifices. The nozzle may form a number of orifices. For example, the nozzle may form up to 10 orifices. Each orifice of the several orifices may have a diameter in a range from about 0.008 inches up to about 0.15 inches. The several orifices may be configured in a polygonal pattern, a circular pattern, or an arcuate pattern. In some embodiments, an orientation of the nozzle with respect to an axis of the laser beam is adjustable, for example, at an angle in a range from about 0° up to about 90° with respect to the laser beam. In some embodiments, the orientation of the nozzle is about 77° with respect to the laser beam.

In some embodiments, a distance between a tip of the nozzle and the area of the dental tissue to be treated is in the range from about 2 millimeters up to about 50 millimeters. The fluid-delivery system may be configured to direct the fluid flow as one or more of a series of droplets, a series of columns, and a mist. The area to be treated may be in a range from about 0.00005 square inches up to about 0.055 square inches, and the dental tissue may include or consist essentially of a hard dental tissue. In some embodiments, an air curtain eliminates or reduces the risk that the cooling fluid after striking the area/region to be treated (e.g., a surface of a tooth) may bounces back and interfere with the laser beam.

In another aspect, various embodiments feature a method for dental tissue treatment. The method includes directing a laser beam to an area of dental tissue to be treated, and directing and controlling a flow of a fluid to at least a portion of the area to be treated to substantially prevent both a change in laser energy absorption by the dental tissue and attenuation of treatment efficiency due to fluid interference with the laser beam.

The flow of the fluid may be controlled. In some embodiments, the method includes controlling the flow of the fluid so as to provide a sufficient amount of fluid to substantially prevent the melting of the dental tissue. The control of the fluid flow may also include limiting an amount of fluid to limit absorption of the laser beam in the fluid.

In some embodiments, the control of the flow of the fluid is performed, at least in part, by using a pressure relief regulator. The method may include pumping the fluid using a positive displacement pump so as to control the fluid flow. In some embodiments, the method includes monitoring the flow of the liquid using a fluid flow switch, and controlling the laser beam if a lack of fluid flow is detected and/or a fluid flow that includes bubbles is detected. The fluid may be delivered using a nozzle forming one or more orifices. An orientation of the nozzle with respect to an axis of the laser beam may be adjusted to direct the coolant fluid to a selected spot within the area of treatment. A hard dental tissue may be treated in some embodiments.

BRIEF DESCRIPTION OF THE DRAWINGS

The present invention will become more apparent in view of the attached drawings and accompanying detailed description. The embodiments depicted therein are provided by way of example, not by way of limitation, wherein like reference numerals refer to the same or similar elements. The drawings are not necessarily to scale, emphasis instead being placed upon illustrating aspects of the invention. In the drawings:

FIG. 5 is a table of various parameters used to control the fluid flow according to various embodiments;

DETAILED DESCRIPTION

A process is disclosed that combines a laser based dental treatment system with a controlled delivery of cooling fluid. The laser based system may be computer controlled and the coolant fluid delivery system may include an air curtain to limit the amount of cooling fluid that could interfere with the laser beam.

Figure 1:
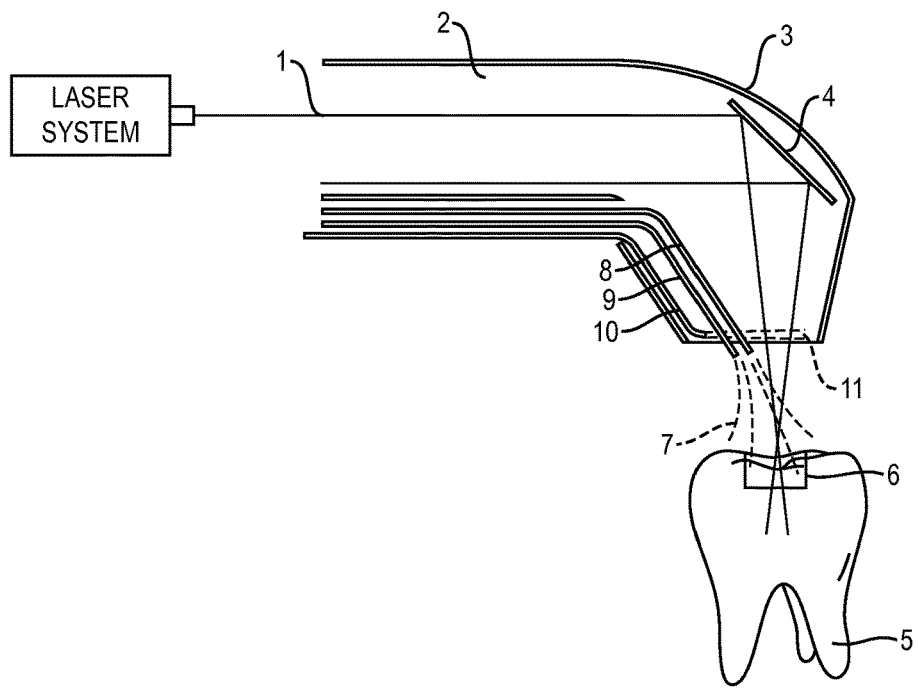
FIG. 1 show a cross sectional view of a tooth and an exemplary process of supplying a cooling fluid via a fluid delivery system according to one embodiment.

FIG. 1 depicts one embodiment in which a laser beam 1 emerges from a hand piece 2, which is a part of the laser treatment/cutting system 3. The laser beam can be computer controlled, and is reflected off a mirror 4 to perform the cutting operation on the tooth 5 or other tissue The user can select the geometry of the cut 6 and the depth of the cut 6. Cooling fluid 7 is directed to the tooth 5 via nozzles 8 and 9. This fluid provides both the critical cooling needed to fully control the cutting but also helps to remove the cut material from the tooth 5. A separate nozzle assembly 10 supplies an air curtain 11 that may keep the cooling fluid from splashing back into the hand piece 2. The separate nozzle assembly 10 is designed to supply a controlled amount of air to form the air curtain 11 that is substantially a laminar flow. This can minimize the disruption to the laser beam 1. The flow of the coolant fluid is generally controlled such that the cuts, such as cut 6, can be achieved consistently and in a repeatable manner using the laser beam 1.

Figure 2:
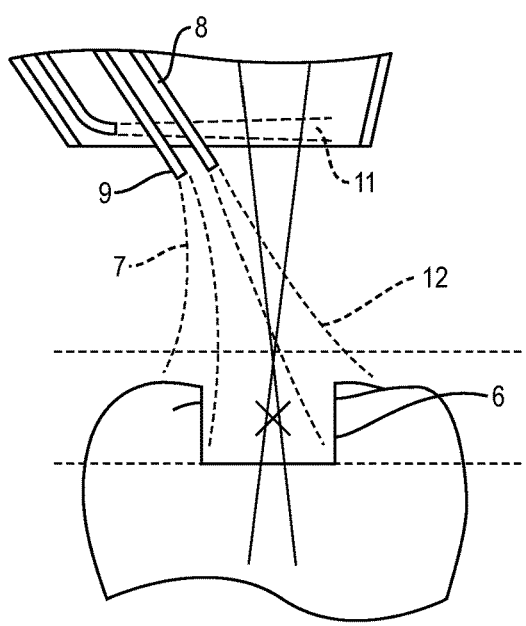
FIG. 2 shows another cross sectional view of the tooth as the cutting process continues creating a controlled cut profile, according to one embodiment.

FIG. 2 depicts a section of the tooth 5 when the cut 6 is in progress. The laser beam 1 is focused on only a portion of the cut 6 and is scanned to achieve the final geometry and depth of that cut 6. The fluid flows 7, 12 are delivered from nozzles 9, 8 respectively and are directed and controlled by the design of the nozzles 9, 8. In particular, the aperture size of the nozzles and their orientation are selected according to one or more of the parameters shown in FIG. 5. The orientation of the nozzles can determine the angle at which the fluid spray from the nozzle impinges a dental surface to be treated.

In some embodiments, the flows 7, 12 of the cooling fluid are controlled differently as the cut 6 gets deeper. It is beneficial to provide an adequate amount of cooling fluid from the flows 7, 12 to the bottom of the cut 6, so as to substantially prevent melting of the enamel at the bottom. As the cut 6 becomes deep, this can be accomplished by changing the flow pattern from droplet or mist, which may be suitable when the treatment region is generally flat, to a fluid column when the cut is deep. The flow pattern may be changed by varying the pressure of the gaseous fluid. Generally, lower gas pressures provide a droplet flow pattern, slightly higher gas pressures provide a column of coolant, and higher gas pressures provide a mist, with the highest gas pressures providing the finest mist. Varying the gas pressure may be computer controlled through the use of an electric regulator, for example an SMC ITV-0030-3UBS electric regulator. Pooling of the coolant fluid at the bottom of the cut 6 can be avoided, however. This can be achieved, in part, by delivering the column of fluid intermittently, such as in a pulsed pattern. In addition or alternatively, a droplet or a beam of a coolant liquid and a bust of a gas (such as air)

can be alternately delivered to the cut 6, so as to provide adequate wetting and cooling while minimizing or avoiding pooling of the liquid.

Figure 3:
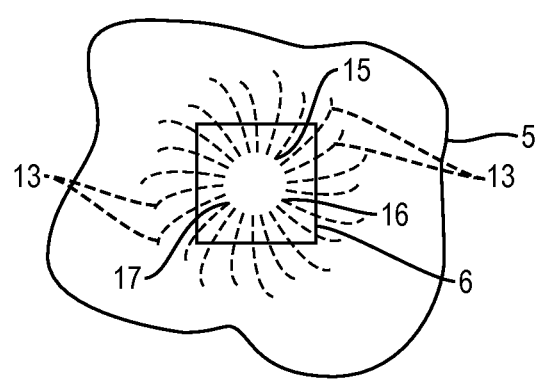
FIG. 3 shows a plan view of a section of the tooth with a square cut region and delivery of the coolant fluid to the cut region, according to one embodiment.

FIG. 3 shows a view looking down on a surface of the tooth 5 with the square cut 6. In order to sufficiently cool the entire cut region 6, the coolant flow 13 can be delivered in a uniform manner (e.g., with a variation of the amount of fluid delivered during at least a part of the treatment less than 2%, 5%, 15%, etc.) throughout the geometry of the cut 6. This can be achieved, in part, by delivering the coolant fluid as a mist, or by delivering the coolant via different orifices of the nozzle at different times, to target different locations 15, 16, 17 of the cut region 6. In order to target different locations multiple fluid conduits may fluidically connect different nozzles with a single pump via different switching valves, or different nozzles may be in fluidic communication with a corresponding pump in a set of pumps.

Figure 4A:
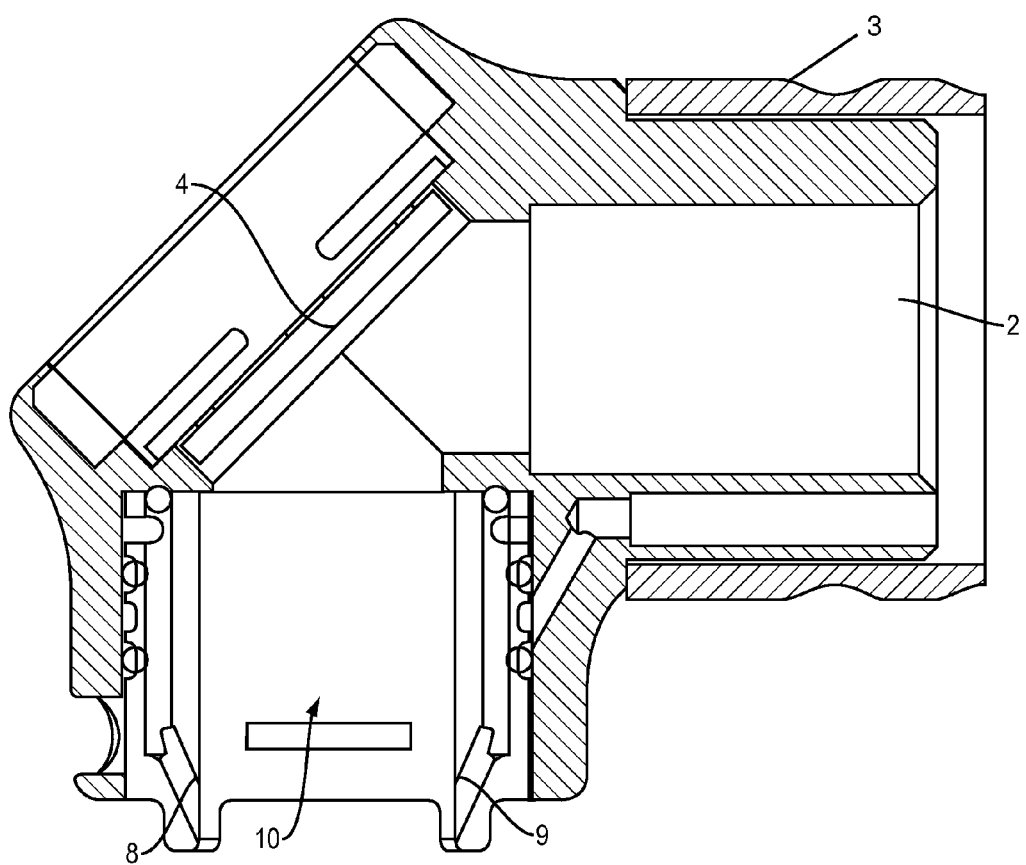
FIGS. 4A-4D depict various exemplary nozzles, according to different embodiments.
Figure 4B:
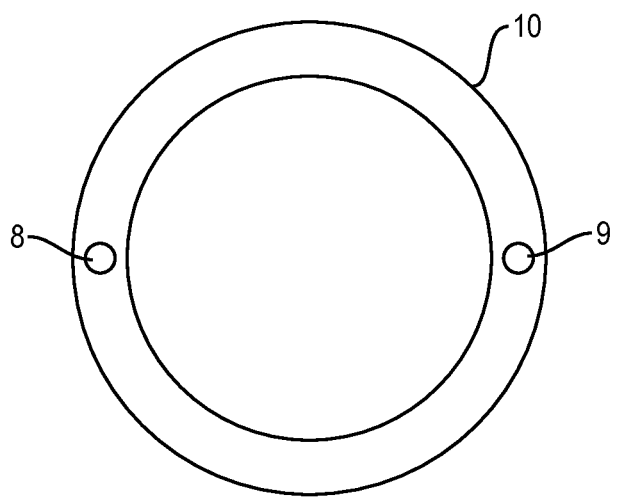
Figure 4C:
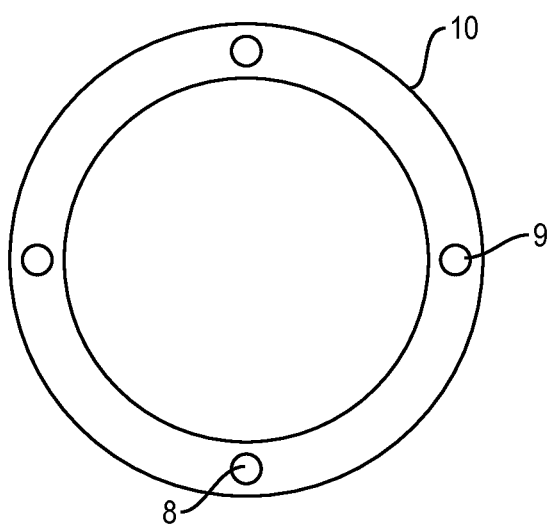
Figure 4D:
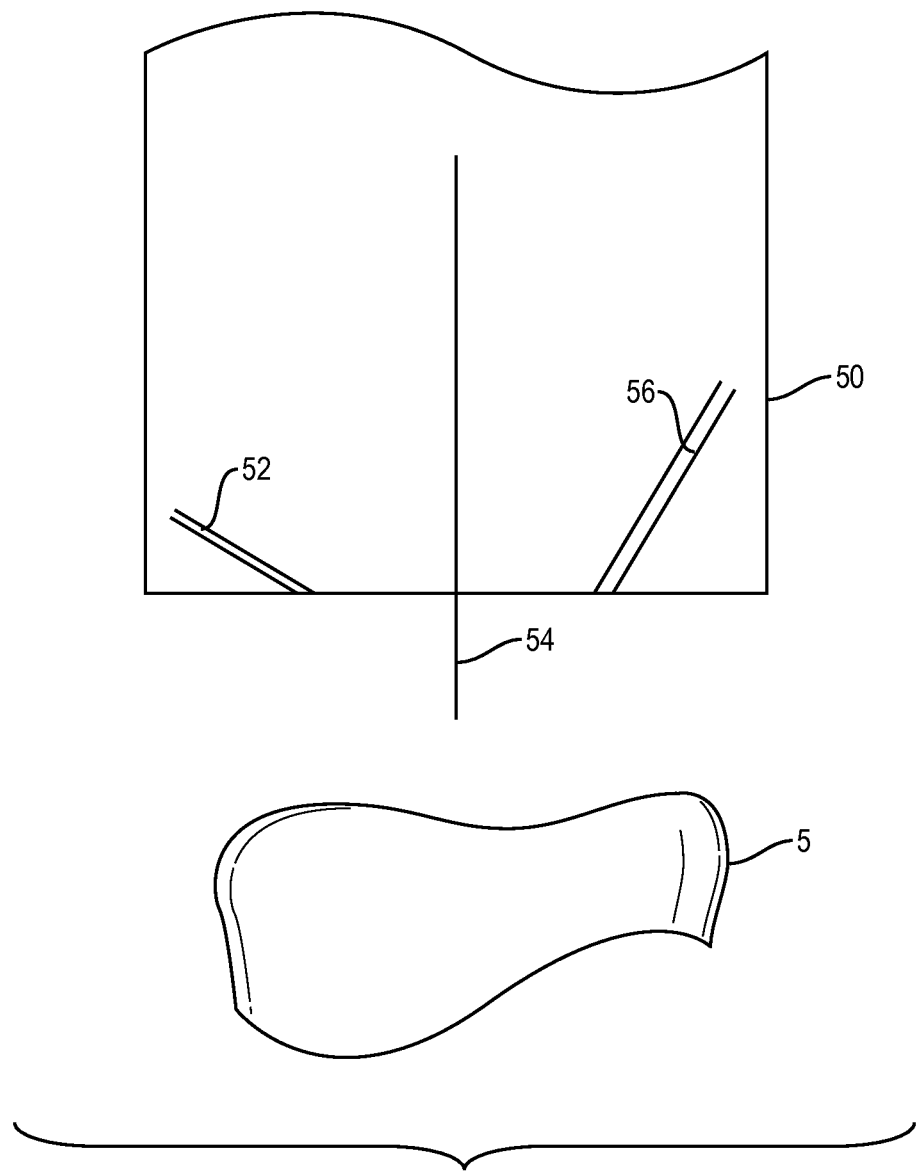

FIGS. 4A-4C show a cross-section of a typical 5-15 μm dental laser hand-piece, and a cross-sections of two exemplary nozzles, respectively. The hand-piece 3 encloses the beam path 2 and the 45 degree turning mirror 4. The nozzle assembly 10 is inserted into the hand-piece 3 and the cross-section shows typical misting nozzles 8, 9. Fluid, i.e., a liquid, a gas, or a mixture thereof can be delivered through the nozzles 8, 9. In some embodiments, liquid (e.g., water) may be delivered through one nozzle (e.g., nozzle 8) and a gas (e.g., air) may be delivered through the other nozzle (e.g., nozzle 9). As depicted in FIG. 4B, the nozzle assembly has two orifices in a rim. The nozzle assembly depicted in FIG. 4C has four orifices. In general, a nozzle assembly may have as few as one orifice and more than four (e.g., 6, 8, 10, etc.) orifices, so as to control one or more individual fluid flows and/or the fluid flow resulting from the combination of the flows through each orifice. FIG. 4D depicts an embodiment of a nozzle assembly 50 that includes a nozzle 52 oriented at an angle of about 77° with respect to an axis of the laser beam 54. The nozzle assembly 50 includes another nozzle 56 oriented at an angle of about 30° with respect to the axis of the laser beam 54. A controller may select the coolant fluid flow via the nozzle 52 at one time during a dental treatment and via the nozzle 56 at another time during the dental treatment. Even though the nozzle assembly 50 includes only two nozzles, this is illustrative only. In general, a nozzle assembly may include more than two nozzles, each of which or groups of which are oriented at different angles with respect to the axis of the laser beam. Each nozzle or groups of nozzles may be selected to deliver the coolant flow at different times during the dental treatment.

Various parameters of the system, e.g., pressure and flow rate of a gas and a liquid that may be combined in a nozzle to form a mist, a droplet, or a column, may be adjusted and controlled during the treatment. The various parameters used to control the fluid flow are depicted in FIG. 5. The cooling fluid may further be treated with surfactants or other chemicals that are safe for use in dental treatment, and that can enhance the removal of enamel and/or assist in maintaining a thin uniform layer of the cooling fluid in the area of the cut.

Figure 6:
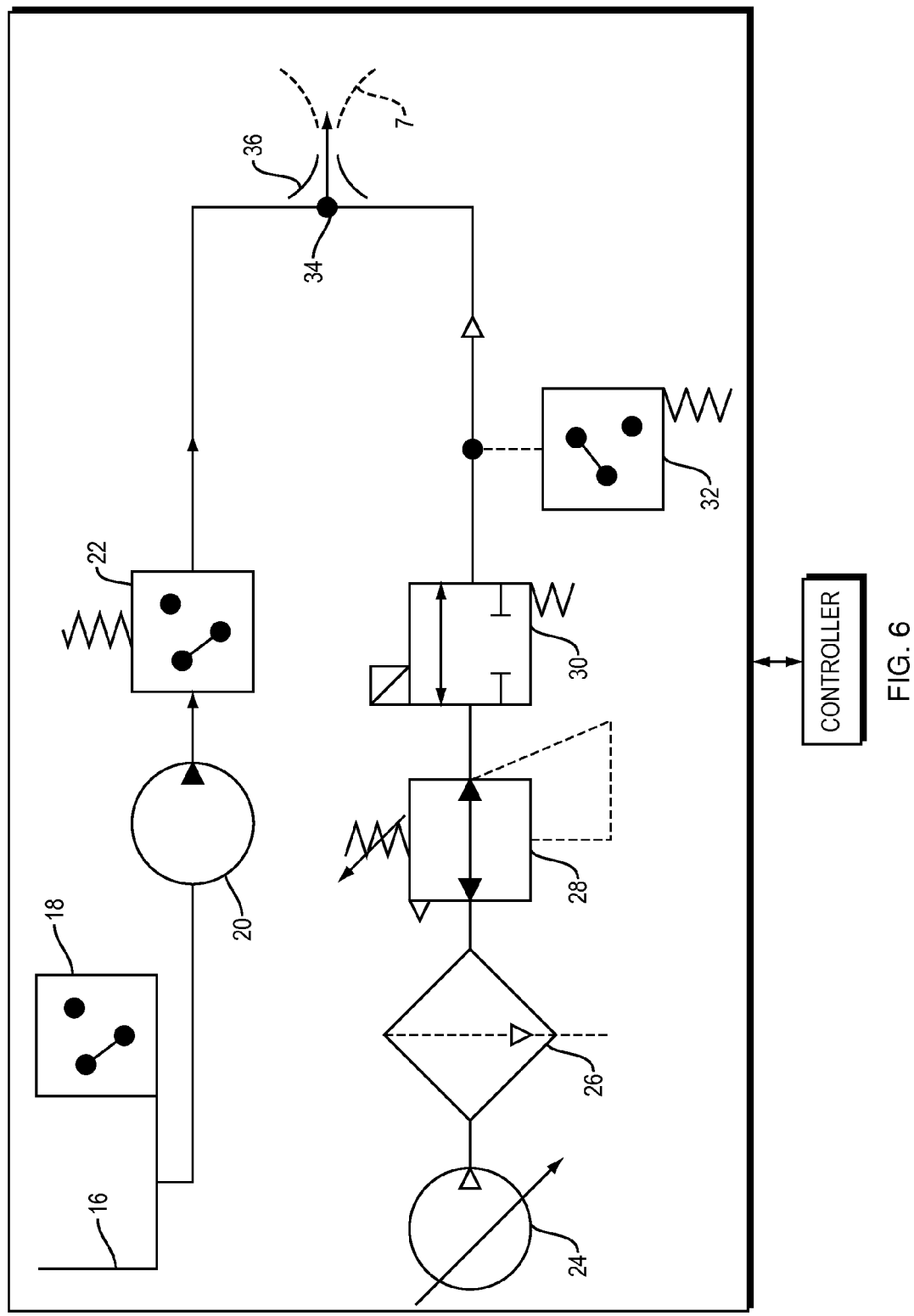
FIG. 6 schematically depicts a fluid delivery system in which the fluid includes both a liquid and a gas, according to on embodiment.

FIG. 6 schematically illustrates a fluid delivery system that provides fluids to the laser treatment area. The liquid fluid is stored in a vented reservoir 16. The treatment system is notified when liquid coolant is low, by a liquid level switch 18. An example of a suitable liquid level switch is the pairing of a magnetic float, such as MEDER Item No: 2500000026 within the reservoir and a normally open reed switch, such as MEDER Item No: 2242711054 that closes when the float is proximate (e.g., in contact with or within a few millimeters from the reed switch). Coolant/water is pumped from the vented reservoir 16, using a positive displacement pump 20. The use of the positive displacement pump 20 allows for control of the liquid fluid flow rate as that rate is generally proportional to the rotational velocity of the pump 20. In general, the higher the rotational velocity of the positive displacement pump 20 the greater the flow rate of the liquid fluid and the greater the quantity of the liquid fluid delivered to the treatment area.

A peristaltic pump is an example of a positive displacement pump that is well suited for a fluid delivery system, because the wetted surfaces of the pump are usually limited to a tube within the pump. An FDA compliant tubing may be used within the peristaltic pump. An example of a peristaltic pump that is suitable for a fluid delivery system is a Boxer 9000 paired with a 375 rpm motor and 2 mm I.D. PharMed BPT biocompatible tubing. Because the flow of liquid fluid is needed to sufficiently cool the treatment area and to substantially prevent melting and thermal damage of the hard tissue, a fluid flow switch 22 can be used to ensure a flow of the liquid fluid to the treatment area. The Sensirion LG01 is an exemplary flow switch used in the system illustrated with reference to FIG. 6. In addition to detecting the liquid fluid flow the switch 22 can also detect the presence of bubbles that could potentially cause intermittent misting or delivery of the liquid fluid. If complete and/or partial interruption (e.g., due to a large number of bubbles) is detected in the liquid flow, the operation of the laser beam can be turned off manually and/or automatically to prevent any damage to the treatment area.

The coolant fluid in the exemplary system shown in FIG. 6 also includes a gas, which is air in one embodiment. In general, the coolant fluid may not include any gas, or may include gases other than air. An air compressor 24 supplies the air. A compressor that is small enough so that it can be positioned inside the housing for the laser device can provide sufficient pressure and flow. Additionally or in the alternative, an external air compressor may be used with the fluid delivery system. The Gardner Denver Thomas 415ZC36/24 is an exemplary air compressor. The air may be filtered and dried using an air filter 26 such as the SMC AF20-NO2C-CZ air filter with automatic drain.

The pressure of the air is regulated by using a pressure relief regulator 28. By changing the pressure of the gaseous fluid, the liquid fluid may be jetted in the form of a droplet at very low or low gas pressure (e.g., from about 0 psi up to about 5 psi), a column at low or medium gas pressure (e.g., from about 5 psi up to about 15 psi), or mist at high gas pressure (e.g., from about 15 psi up to about 80 psi). The aeration of the mist can be further controlled by the regulated pressure of the gaseous fluid, such that the higher the gas pressure the finer the mist. The SMC NARM1000-2A1-N01G is an exemplary air regulator suitable for some embodiments of the fluid delivery system.

In the system shown in FIG. 6, the gas pressure at the nozzle orifices 36 is controlled by a normally closed solenoid valve 30, e.g., the SMC VQZ115-5L1-01T valve. By opening this valve, air is supplied to the nozzle 10 to form a mist. Providing a regulated air pressure to the mist nozzle along with a regulated flow of liquid coolant can produce a jet of aerated coolant that has repeatable flow, form, and cooling properties. For example, an air pressure around 20 gauge psi can provide a uniform mist over a broad range of water flow rates. A water flow rate of about 6.9 ml/min can provide sufficient cooling for many hard tissue dental treatments with moderate laser power. The water flow rate may be reduced to as low as about 2 ml/min and increased to as high as about 10 ml/min by the operator (e.g. a dentist) to achieve a high quality cut. The change in water flow rate can be made independently of the air pressure setting. Generally, low water flow rates may be used for treatment of pulp, dentin, or soft tissue because the laser is typically operated at less power than that used to cut hard tissue and, as such, the need for cooling will be less. High water flow rates may be generally used with laser power at a high setting, for the treatment of hard tissue such as enamel. The greater the water flow rate the greater the cooling of the treatment area/region.

The laser system can ensure that gas/air pressure is present in the nozzle 10 when the solenoid valve 30 is open by monitoring the gas/air flow with a pressure switch 32 located on the opposite side of the solenoid valve 30 than the side on which the compressor 24 is located. The pressure switch, 32, (e.g., the SMC PS 1000-R07L) may indicate to the laser system whether the air pressure is above a set threshold. If the air pressure is below a certain specified threshold, the laser system may be shut down manually and/or automatically.

In the fluid delivery system depicted in FIG. 6, the gas (e.g., air) and liquid fluid (e.g., water) are combined in a mixing chamber 34 in the misting nozzle head and then jetted out of one or more orifices 36. In the embodiments that use more than one orifice, smaller more restrictive orifices can provide a more evenly distributed mist. The fluid delivery system may include an independent controller or may be controlled by the laser system controller.

Various embodiments of a system and method described above may use a laser that has a wavelength between about 5 and 15 µm and that can directly interact with a major constituent of the tooth enamel thereby cutting that enamel rapidly and with smaller energy pulses compared to the lasers conventionally used in dental treatment, allowing more precision than the conventional burr and laser based systems. The various embodiments allow for a controlled delivery of precise volumes of the cooling fluids in selected portions of treatment areas, while minimizing the interactions of the cooling fluid with the laser beam. The thin film may provide sufficient cooling while allowing a significant portion of the laser beam energy to be absorbed in the material to be ablated.

In some embodiments, the cooling fluid is directed precisely into the cut area of the tooth while avoiding interference of the fluid with the laser beam. This is particularly beneficial regardless of the type of laser used, because as the cut deepens it usually becomes more difficult to get the cooling fluid into the cut area of the tooth, and it also usually becomes difficult to minimize pooling of the coolant in the cut region, and the pooled coolant can interfere significantly with the laser beam. To this end, using one or more fluid controllers such as valves, pressure switches, fluid flow switches, and pressure regulators, pumps, and nozzles, the form and amount of the coolant fluid present in the region of treatment can be controlled such that the coolant fluid can form a thin uniform film of the fluid on the area/region to be treated (e.g., a surface of a tooth), and such that the fluid does not pool into large drops. Treating the coolant fluid with surfactants can lower the surface tension of the fluid, which can reduce the undesirable pooling of the fluid. The use of a surfactant is beneficial if the cooling fluid, e.g., is water. In some embodiments, an additional nozzle can provide an air curtain using a controlled flow of pressurized air, to reduce the likelihood that the coolant fluid may splash back after hitting the tooth being treated. The air curtain system may be designed to provide a substantially laminar airflow so as to limit back splash of the cooling fluid.

Using an embodiment of a system and/or method that include one or more of the above described features can lead to a high degree of control of the overall dental procedure, increasing the safety and comfort of the patient. Together, a laser with a wavelength of about 5 to about 15 µm and a control system for regulating the coolant fluid delivery can enable an operator to cut precise user-defined patterns into the tooth. Thus, the fluid delivery control system provides to an operator (e.g. a dentist) the ability to establish a cutting geometry that is best suited to a particular tooth (i.e., shape, size, general health/condition of the tooth) and to the type of treatment.

Figure 7:
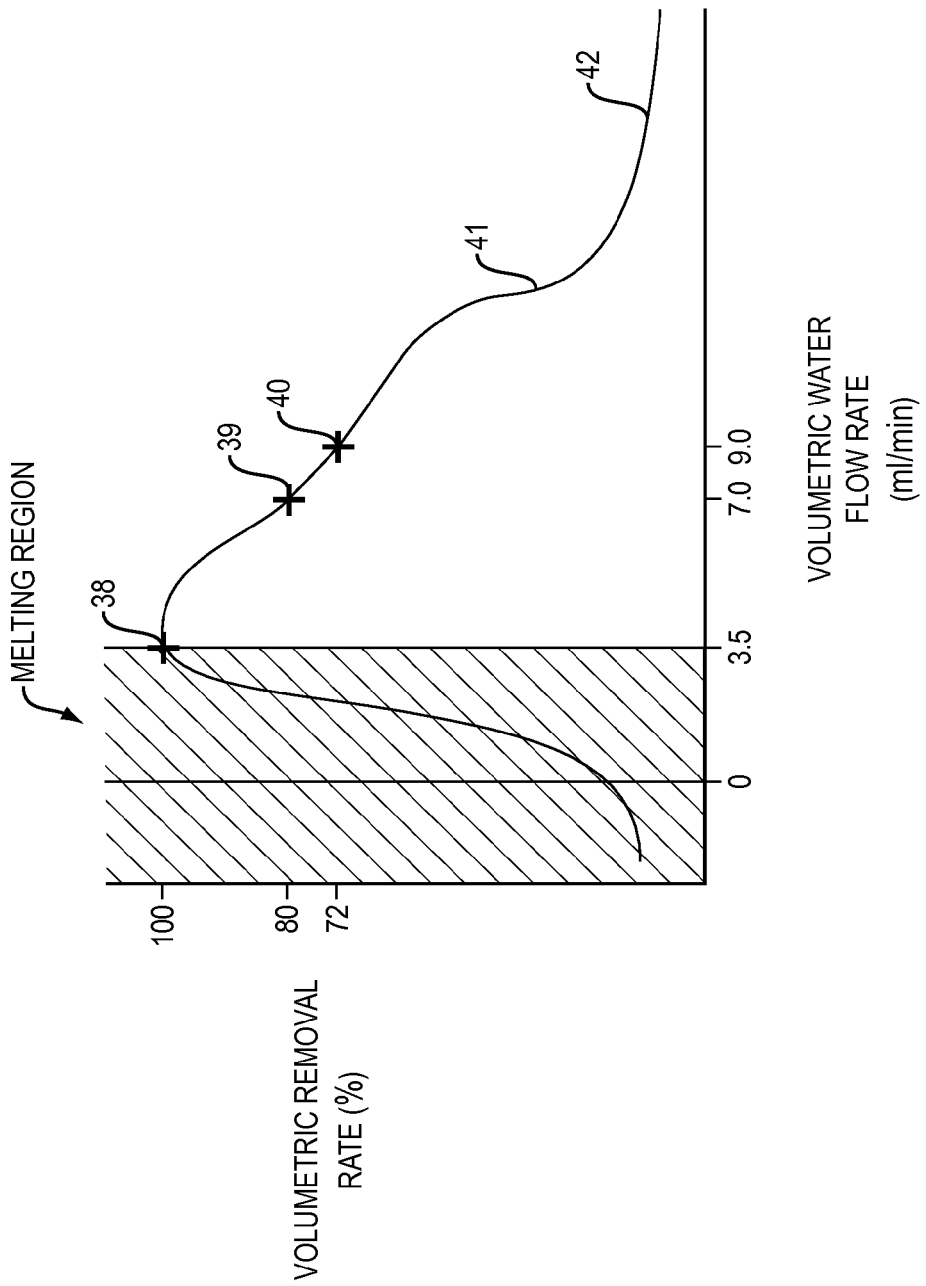
FIG. 7 depicts a relationship between volumetric flow rate of a coolant and hard tissue removal rate, according to one embodiment.

FIG. 7 depicts an exemplary enamel/hard tissue ablation performance curve. The volumetric removal rate is displayed on the Y-axis and the volumetric flow rate of the coolant (e.g., a water air mist) is displayed on the X-axis. Near the Y-axis is a melting region 37 where the volumetric flow rate is low (typically less than 2 ml/min). The volumetric removal rates in the melting region is very low—generally less than 20% of the optimized removal rate (e.g., about 0.25 mm$^3$/s). As the volumetric flow rate of the coolant is increased (e.g., up to about 3.5 ml/min), the temperature of the surface of the enamel/hard tissue decreases and the undesired melting is eliminated or reduced significantly. When the surface melting is eliminated ablation dominates and the enamel/hard tissue removal rate is maximized, e.g., about 0.25 mm$^3$/s, as shown at 38.

As the volumetric flow rate of the coolant is further increased (e.g., up to about 7 ml/min), the enamel/hard tissue surface temperature continues to stay below the melting point, so ablation continues. But the additional amount of coolant present in the treatment area/region begins to absorb increasing amounts of laser energy and, as such, the removal rate begins to decrease. At a coolant flow rate of about 7 ml/min, the removal rate drops to about 80% of the peak or optimized removal rate, as depicted at 39. As the volumetric flow rate continues to increase (e.g., up to 20 ml/min) the coolant absorbs a large portion of the laser energy and an amount of laser radiation energy required to cause ablation is not absorbed in the enamel/hydroxyapatite. The volumetric removal rate decreases significantly as shown at 41 to about 15% of the peak removal rate depicted at 38, and may remain low or decrease further as depicted at 42.

With reference to FIG. 7, a change in laser energy is substantially prevented when the volumetric flow rate of the coolant fluid corresponds to the peak removal rate at 38. In contrast, the absorption of laser energy by the hydroxyapatite is significantly affected if the flow rate of the coolant corresponds to the melting region and/or to the removal rates at 41, 42. The treatment efficiency (e.g., a percentage change in the removal rate relative to the optimized removal rate) is significantly attenuated in the melting region due to lack of adequate cooling. The treatment efficiency corresponding to the removal rates at 39, 40 is attenuated, and corresponding to the removal rates at 41, 42 is significantly attenuated, due to interference by the cooling fluid present in the treatment area/region. In general, cutting efficiency can be expressed in terms of time required to perform the procedure, dental material removal rate, amount of melting occurred, quality of the cut in terms of shape, fineness, etc., required skill to perform the cut, and a combination of two or more of these parameters. The cutting efficiency may be controlled by adjusting one or more of the various parameters listed in FIG. 5.

An exemplary cut in the enamel/hard tissue (about 2 mm×2 mm×2 mm in volume) at differing coolant flow rates illustrates the effect excess coolant may have on the efficiency of laser cutting. Cutting this volume of enamel with a minimum of coolant flow rate without causing excessive melting (about 3.5 ml/min) required on an average about 32 seconds and required a highly skilled operator to make a precise cut, in part, due to the presence of debris and some melted enamel. This water flow setting resulted in a material removal rate of about 0.25 mm$^3$/s and is shown as 100% or peak rate 38 in FIG. 7. Cutting substantially the same volume of enamel at a water flow rate of about 7 ml/min required about 40 seconds. Cutting at this flow rate required less skill to make a precise cut and the cut contained less debris and melt than that with the flow rate of about 3.5 ml/min. The material removal rate at this fluid flow setting was observed to be around 0.20 mm$^3$/s and is shown in FIG. 7 at 39, as about 80% of the peak removal rate at 38. The removal of nearly the same volume of enamel/hard tissue at a coolant flow rate of about 9 ml/min required on an average about 44 seconds. The cut contained even less amounts of melt and debris. This coolant flow setting resulted in a material removal rate of about 0.18 mm$^3$/s and can be seen in FIG. 7 at 40, as about 72% of the peak removal rate at 38.

While the invention has been particularly shown and described with reference to specific embodiments, it will be understood by those skilled in the art that various changes in form and detail may be made therein without departing from the spirit and scope of the invention as defined by the appended claims. The scope of the invention is thus indicated by the appended claims and all changes that come within the meaning and range of equivalency of the claims are therefore intended to be embraced.

What is claimed is:

1. An apparatus for dental tissue treatment, the apparatus comprising:
    a laser source for generating a laser beam having a wavelength in a range from 5 µm to 15 µm that is absorbed in hydroxyapatite in dental tissue;
    a system for directing the laser beam to an area of dental tissue to be treated;
    a controller for controlling the laser beam; and
    a fluid-delivery system comprising a fluid flow switch adapted to detect bubbles in a flow of a fluid comprising a liquid,
    the controller being adapted to automatically turn off the laser beam in response to the fluid flow switch detection bubbles in the fluid flow,
    the fluid-delivery system being adapted for directing and controlling the flow of the fluid comprising the liquid to at least a portion of the area to be treated to substantially prevent a change in laser energy absorption by the dental tissue and attenuation of treatment efficiency due to fluid interference with the laser beam.

2. The apparatus of claim 1, wherein the fluid-delivery system is configured to adjust a rate of flow of the liquid.

3. The apparatus of claim 1, wherein the fluid further comprises a gas.

4. The apparatus of claim 3, wherein the fluid-delivery system is configured to adjust a rate of flow of the gas.

5. The apparatus of claim 3, wherein the fluid-delivery system is configured to adjust a pressure of the gas flow in the range from 0 psi up to 80 psi.

6. The apparatus of claim 1, wherein the fluid-delivery system is configured to adjust a rate of flow of the fluid.

7. The apparatus of claim 1, wherein the fluid-delivery system is configured to adjust a pressure of the fluid flow in the range from 0 psi up to 80 psi.

8. The apparatus of claim 1, wherein:
    the fluid-delivery system comprises a positive displacement pump for controlling the flow of the fluid;
    the pump operates at a frequency of up to 750 rpm; and
    the frequency of the pump controls a rate of flow of the liquid.

9. The apparatus of claim 8, wherein the positive displacement pump comprises a peristaltic pump.

10. The apparatus of claim 1, wherein:
    the fluid is delivered using a nozzle forming a plurality of orifices.

11. The apparatus of claim 10, wherein the nozzle forms up to 10 orifices.

12. The apparatus of claim 10, wherein each orifice of the plurality of orifices has a diameter in a range from 0.008 inches up to 0.15 inches.

13. The apparatus of claim 10, wherein the plurality of orifices are disposed about a rim of the nozzle.

14. The apparatus of claim 1, wherein the dental tissue is a hard dental tissue.

15. A method for dental tissue treatment, comprising:
    generating a laser beam having a wavelength in a range from 5 µm to 15 µm that is absorbed in hydroxyapatite in dental tissue;
    directing the laser beam to an area of dental tissue to be treated;
    detecting bubbles in a fluid flow comprising a liquid using a fluid flow switch;
    turning off the laser beam in response automatically with a controller; and
    directing and controlling the flow of the fluid comprising the liquid to at least a portion of the area to be treated to substantially prevent a change in laser energy absorption by the dental tissue and attenuation of treatment efficiency due to fluid interference with the laser beam.

16. The method of claim 15, wherein a rate of flow of the liquid is adjusted.

17. The method of claim 15, wherein the fluid further comprises a gas.

18. The method of claim 17, wherein a rate of flow of the gas is adjusted.

19. The method of claim 17, wherein a pressure of the gas flow is adjusted such that the pressure is in a range from 0 psi up to 80 psi.

20. The method of claim 15, wherein a rate of flow of the fluid is adjusted.

21. The method of claim 15, wherein a pressure of the fluid flow is adjusted such that the pressure is in a range from 0 psi up to 80 psi.

22. The method of claim 15, wherein:
    the controlling the flow of the fluid comprises pumping the fluid using a positive displacement pump;
    the controlling the flow of the liquid comprises operating the pump at a frequency of up to 750 rpm; and
    the frequency of the pump controls a rate of flow of the liquid.

23. The method of claim 22, wherein the positive displacement pump comprises a peristaltic pump.

24. The method of claim 15, wherein:
    the fluid is delivered using a nozzle forming a plurality of orifices.

25. The method of claim 24, wherein the nozzle forms up to 10 orifices.

26. The method of claim 24, wherein each orifice of the plurality of orifices has a diameter in a range from 0.008 inches up to 0.15 inches.

27. The method of claim 24, wherein the plurality of orifices are disposed about a rim of the nozzle.

28. The method of claim 15, wherein the dental tissue is a hard dental tissue.

\* \* \* \* \*